(12) United States Patent
Lampropoulos et al.

(10) Patent No.: US 7,740,608 B2
(45) Date of Patent: Jun. 22, 2010

(54) LOCKING DRAINAGE CATHETER WITH ROTATABLE LEVER HANDLE AND RELEASE TOOL

(75) Inventors: Fred P. Lampropoulos, Salt Lake City, UT (US); Nicholas Gerald Accisano, III, Howell, NJ (US); Garlyn W. Hendry, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 169 days.

(21) Appl. No.: 11/608,518

(22) Filed: Dec. 8, 2006

(65) Prior Publication Data
US 2007/0083189 A1 Apr. 12, 2007

Related U.S. Application Data

(63) Continuation-in-part of application No. 11/081,301, filed on Mar. 16, 2005.

(51) Int. Cl.
*A61M 31/00* (2006.01)
*A61M 25/00* (2006.01)
(52) U.S. Cl. .............. 604/95.05; 604/523; 604/95.04; 604/95.01
(58) Field of Classification Search ... 604/95.01–95.05, 604/541; 33/767
See application file for complete search history.

(56) References Cited

U.S. PATENT DOCUMENTS

| | | | |
|---|---|---|---|
| 1,207,479 | A | 12/1916 | Bisgaard |
| 3,315,592 | A | 4/1967 | Lems |
| 3,513,848 | A | 5/1970 | Winston et al. |
| 3,798,687 | A | 3/1974 | Stevens |
| 3,924,633 | A | 12/1975 | Cook et al. |
| 4,206,910 | A * | 6/1980 | Biesemeyer ............ 269/236 |

(Continued)

FOREIGN PATENT DOCUMENTS

WO WO 2006/098818 9/2006

(Continued)

OTHER PUBLICATIONS

Angiodynamics, Abscession Drainage Catheter: A Quick Guide to the Locking Mechanism, AngioDynamics, Inc., Nov. 1999.

(Continued)

*Primary Examiner*—Nicholas D Lucchesi
*Assistant Examiner*—Ian K Holloway
(74) *Attorney, Agent, or Firm*—Stoel Rives LLP

(57) ABSTRACT

A catheter kit including a drainage catheter hub having a rotatable lever handle adapted to secure a suture thread to maintain the anchor configuration of the distal end of the catheter to secure the position of the catheter within the patient's body. The rotatable lever handle has a released position for allowing movement of the suture and a secured position for preventing movement of the suture. A rotatable lever handle adapted to secure the proximal portion of the suture that may otherwise remain loose during the procedure. The rotatable lever handle and associated rotatable barrel can be depressed relative to hub body in a locked configuration to prevent inadvertent rotational movement of the rotatable lever handle and a release slot or release button that can be actuated by the practitioner with a release tool to allow for rotational movement of the rotatable lever handle.

16 Claims, 15 Drawing Sheets

U.S. PATENT DOCUMENTS

| | | | |
|---|---|---|---|
| 4,573,981 | A | 3/1986 | McFarlane |
| 4,586,923 | A | 5/1986 | Gould et al. |
| 4,643,720 | A | 2/1987 | Lanciano |
| 4,738,667 | A | 4/1988 | Galloway |
| 4,740,195 | A | 4/1988 | Lanciano |
| 4,787,892 | A | 11/1988 | Rosenberg |
| 4,885,503 | A | 12/1989 | Takahashi et al. |
| 5,052,998 | A | 10/1991 | Zimmon |
| 5,074,484 | A | 12/1991 | Kray |
| 5,078,684 | A | 1/1992 | Yasuda |
| 5,213,575 | A | 5/1993 | Scotti |
| 5,308,318 | A | 5/1994 | Plassche, Jr. |
| 5,352,198 | A | 10/1994 | Goldenberg et al. |
| 5,399,165 | A | 3/1995 | Paul, Jr. |
| 5,419,764 | A | 5/1995 | Roll |
| 5,472,435 | A | 12/1995 | Sutton |
| 5,489,269 | A | 2/1996 | Aldrich et al. |
| 5,522,400 | A | 6/1996 | Williams |
| 5,549,331 | A | 8/1996 | Yun et al. |
| 5,666,970 | A | 9/1997 | Smith |
| 5,693,083 | A | 12/1997 | Baker et al. |
| 5,704,926 | A | 1/1998 | Sutton |
| 5,730,724 | A | 3/1998 | Plishka et al. |
| 5,806,202 | A * | 9/1998 | Blackman et al. ............. 33/767 |
| 5,893,880 | A | 4/1999 | Egan et al. |
| 5,904,648 | A | 5/1999 | Arndt et al. |
| 6,159,177 | A * | 12/2000 | Amos et al. ............. 604/95.04 |
| 6,165,183 | A | 12/2000 | Kuehn et al. |
| 6,231,542 | B1 | 5/2001 | Amos et al. |
| 6,358,271 | B1 | 3/2002 | Egan et al. |
| 6,454,740 | B1 | 9/2002 | Mody |
| 6,508,789 | B1 | 1/2003 | Sinnott et al. |
| 6,547,761 | B2 | 4/2003 | Liu |
| 6,673,060 | B1 | 1/2004 | Fleming, III |
| 6,699,233 | B2 | 3/2004 | Slanda et al. |
| 7,087,038 | B2 | 8/2006 | Lee |
| 7,217,256 | B2 | 5/2007 | Di Palma |
| 7,578,814 | B2 | 8/2009 | Accisano et al. |
| 2004/0059293 | A1 | 4/2004 | Chu et al. |
| 2005/0070821 | A1 | 3/2005 | Deal et al. |
| 2005/0107739 | A1 | 5/2005 | Palma |
| 2005/0203485 | A1* | 9/2005 | Lee ............................ 604/523 |
| 2006/0206096 | A1 | 9/2006 | Accisano et al. |
| 2006/0212009 | A1 | 9/2006 | Accisano et al. |
| 2006/0217667 | A1 | 9/2006 | Accisano et al. |
| 2007/0032779 | A1 | 2/2007 | Accisano et al. |
| 2008/0097394 | A1 | 4/2008 | Lampropoulos |

FOREIGN PATENT DOCUMENTS

| | | |
|---|---|---|
| WO | WO 2006/098819 | 9/2006 |
| WO | WO 2006/101592 | 9/2006 |
| WO | WO 2007/019074 | 2/2007 |

OTHER PUBLICATIONS

International Search Report and Written Opinion, PCT/US06/03021, mailed Sep. 18, 2007, Accisano et al.
International Search Report and Written Opinion, PCT/US06/03464, mailed Jul. 26, 2007, Accisano et al.
International Search Report and Written Opinion, PCT/US06/03467, mailed Jun. 14, 2006, Accisano et al.
International Search Report and Written Opinion, PCT/US06/29304, mailed Feb. 21, 2007, Accisano et al.
Office Action issued May 28, 2008 in co-pending U.S. Appl. No. 11/078,140.
Interview Summary issued Nov. 25, 2008 in co-pending U.S. Appl. No. 11/078,140.
Amendment and Response to Office Action filed Nov. 26, 2008 in co-pending U.S. Appl. No. 11/078,140.
Statement of Substance of Interview filed Dec. 22, 2008 in co-pending U.S. Appl. No. 11/078,140.
Final Office Action issued Mar. 3, 2009 in co-pending U.S. Appl. No. 11/078,140.
Interview Summary issued Jul. 7, 2009 in co-pending U.S. Appl. No. 11/078,140.
Amendment After Final and RCE filed Sep. 3, 2009 in co-pending U.S. Appl. No. 11/078,140.
Office Action issued Sep. 4, 2008 in co-pending U.S. Appl. No. 11/198,642.
Amendment and Response filed Dec. 19, 2008 in co-pending U.S. Appl. No. 11/198,642.
Interview Summary issued Dec. 23, 2008 in co-pending U.S. Appl. No. 11/198,642.
Statement of Substance of Interview filed Jan. 23, 2009 in co-pending U.S. Appl. No. 11/198,642.
Notice of Allowance issued Apr. 20, 2009 in co-pending U.S. Appl. No. 11/198,642.
Issue Notification issued Aug. 5, 2009 in co-pending U.S. Appl. No. 11/198,642.
Request for Continued Examination filed Aug. 24, 2009 in co-pending U.S. Appl. No. 11/198,642.
Final Office Action issued Mar. 10, 2009 in co-pending U.S. Appl. No. 11/081,301.
Amendment and Response filed Dec. 29, 2008 in co-pending U.S. Appl. No. 11/081,301.
Office Action issued Jun. 26, 2008 in co-pending U.S. Appl. No. 11/081,301.
Amendment filed Apr. 23, 2008 in co-pending U.S. Appl. No. 11/081,301.
Office Action issued Oct. 23, 2007 in co-pending U.S. Appl. No. 11/081,301.
Notice of Allowance issued Aug. 5, 2009 in co-pending U.S. Appl. No. 11/078,939.
Amendment and Response filed Mar. 10, 2009 in co-pending U.S. Appl. No. 11/078,939.
Notice of Non-Compliant Amendment issued Jan. 12, 2009 in co-pending U.S. Appl. No. 11/078,939.
Statement of Substance of Interview filed Jan. 2, 2009 in co-pending U.S. Appl. No. 11/078,939.
Interview Summary issued Dec. 2, 2008 in co-pending U.S. Appl. No. 11/078,939.
Proposed Amendments filed Nov. 21, 2008 in co-pending U.S. Appl. No. 11/078,939.
Office Action issued May 21, 2008 in co-pending U.S. Appl. No. 11/078,939.
Office Action issued May 6, 2009 in co-pending U.S. Appl. No. 11/507,777.
Interview Summary issued Jul. 17, 2009 in co-pending U.S. Appl. No. 11/507,777.
Amendment and Response filed Aug. 6, 2009 in co-pending U.S. Appl. No. 11/507,777.

* cited by examiner

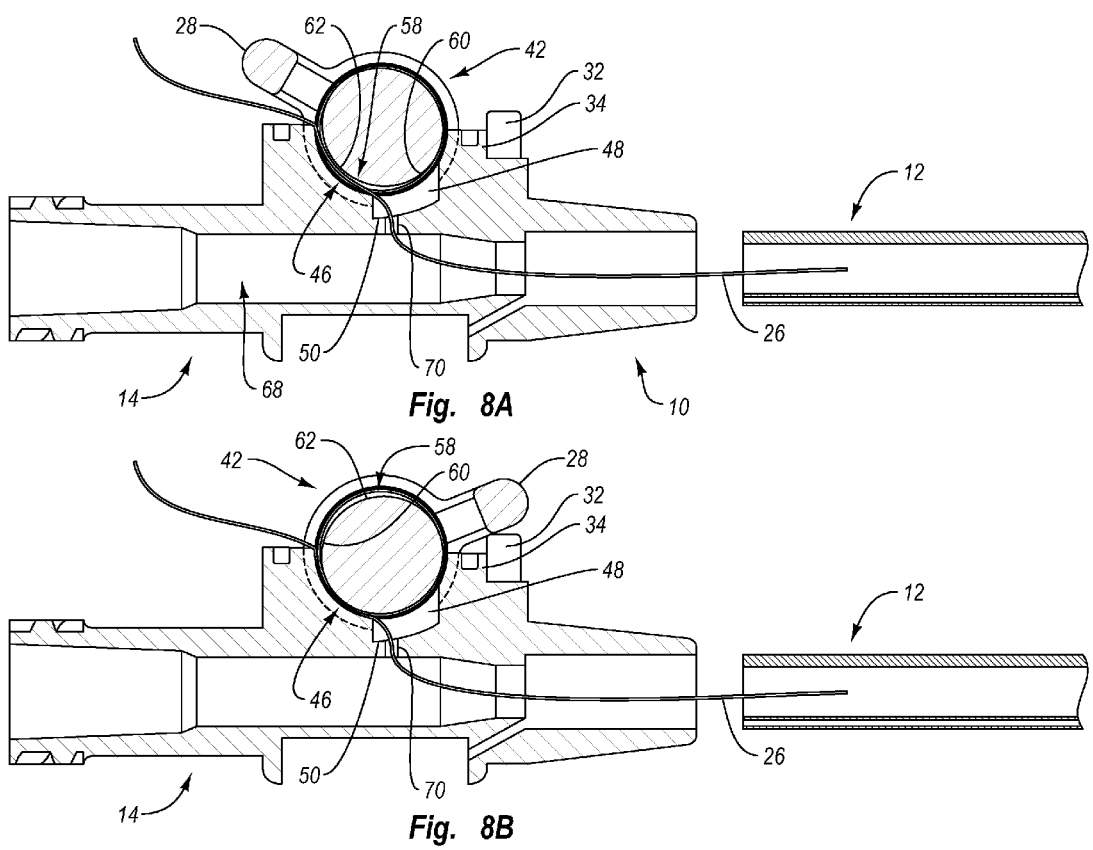

LOCKING DRAINAGE CATHETER WITH ROTATABLE LEVER HANDLE AND RELEASE TOOL

CROSS-REFERENCE TO RELATED APPLICATIONS

This application is a continuation-in-part and claims the benefit of U.S. patent application Ser. No. 11/081,301, filed on Mar. 16, 2005, entitled DRAINAGE CATHETER HUB WITH ROTATABLE LEVER HANDLE, which is expressly incorporated by reference in its entirety by this application.

BACKGROUND OF THE INVENTION

The present invention relates to catheters. In particular, the present invention relates to a catheter kit including, a drainage catheter with a locking hub adapted to secure a suture thread to maintain an anchor configuration at a distal end of the catheter, and a tool for unlocking the locking drainage catheter hub.

One problem often encountered in modern medicine relates to volumes of fluids that collect in a patient's tissue, body cavities, or other positions within a patient's body that exceed normal volumes. Collected fluids can contribute to infection, exert harmful pressure on the patient's organs, or otherwise impede the proper care and recovery of a patient. Drainage catheters have long been utilized to drain such excess volumes of fluids from a patient's body. Typically, the catheter is adapted to be introduced into the patient to the site where the excess fluid is accumulated. A plurality of drainage bores are positioned in the distal end of the catheter to allow passage of the fluids and any materials suspended in the fluids from the volume of fluid to the drainage bore of the catheter.

The distal ends of drainage catheters are typically adapted to form an anchor configuration to secure the drainage catheter at the site where excess fluid is accumulated. However, the tissue surrounding drainage sites often does not provide a solid or reliable substrate to maintain the position of the catheter. As a result, the anchor configuration of the catheter is typically formed in a relatively large pigtail type loop that provides a reliable anchor regardless of the characteristics of the surrounding tissue. The pigtail loop is formed by curling the tip of the catheter tube such that the tip of the catheter contacts a more proximal position on the catheter tube. This is accomplished utilizing a suture that is threaded between the proximal position and the tip of the catheter. When the suture is foreshortened, the tip of the catheter is securely positioned relative to the proximal position on the catheter tube. The portion of the distal end of the catheter tube between the tip of the catheter and the proximal position where the suture exits the catheter tube forms a resulting pig-tail type loop.

The suture is adapted to run the length of the catheter and exit the catheter at the proximal end of the catheter tube. This allows the user to manipulate the suture to maintain or release the anchor configuration of the distal end of the catheter while the distal end of the catheter is positioned inside the patient. Once the anchor configuration of the distal end of the catheter has been established, the practitioner secures the suture to maintain the anchor configuration of the catheter. Otherwise, inadvertent movement of the patient could pull the suture resulting in separation between the tip of the catheter and the proximal position on the catheter tube where the tip of the catheter tube is secured by the suture. Conventionally, a practitioner wraps or ties the free portion of the suture around the proximal portion of the catheter or proximally positioned catheter hub. However, wrapping or tying of the suture can be somewhat inconvenient to perform and make it difficult to release, reposition the anchor, or withdraw the drainage catheter.

A number of devices have been developed to attempt to secure the suture to maintain the anchor configuration of the distal end of the drainage catheter. One device provides a catheter hub adapted such that the suture is threaded between a proximal portion and a distal portion of the hub. To secure the suture, the proximal portion and the distal portion of the hub are pushed toward one another resulting in clamping of the suture between the proximal portion and the distal portion, minimizing movement of the suture. A number of deficiencies are presented by currently available suture securement devices. Many such devices are difficult to manipulate while manually maintaining tension on the suture thread. Additionally, such devices may provide ease in securing the suture, but are not as easily released to allow subsequent manipulation of the suture. Other devices are not intuitive to practitioners utilizing the devices requiring training or leading to improper usage of the device. Some devices do not effectively secure the suture leading to slippage or undesired placement of the distal end of the catheter within the patient. In some cases, the patient may disturb the suture, leading to problems with the drainage catheter that may require reinsertion or other procedures.

What is needed is an easy-to-use locking hub for sutures in a drainage catheter that can be adjusted by a practitioner and cannot be disturbed or adjusted by the patient either on purpose or accidentally.

BRIEF SUMMARY OF AN EMBODIMENT OF THE INVENTION

The present invention relates to catheters. In particular, the present invention relates to a catheter kit including, a drainage catheter with a locking hub adapted to secure a suture thread to maintain an anchor configuration at a distal end of the catheter, and a tool for unlocking the locking drainage catheter hub. The locking hub also has a rotatable lever handle to selectively release and secure the suture thread. The rotatable lever handle has a released position for allowing movement of the suture and a secured position for preventing movement of the suture.

A practitioner positions the rotatable lever handle in the release position for positioning the distal end of the catheter tube in a desired position within a patient's body, such as a volume of bodily fluid to be drained. In the released position, the distal end of the catheter can be configured in a linear or straightened configuration without being restrained by the suture. Once the distal end of the catheter tube is positioned in the desired location within the patient's body, the practitioner grasps the proximal end of the suture and pulls in a rearward direction. This shortens the suture, drawing the tip of the catheter tube in a curved position so that an anchor loop is formed in the distal end of the catheter tube. The anchor loop prevents removal of the distal end of the catheter from the desired position in the patient, minimizing risk of injury.

Once the distal end of the catheter is formed into an anchor loop, the user rotates the rotatable lever handle of the catheter hub to the secured position to maintain the desired positioning of the distal end of the catheter tube within the patient. In the secured position, movement of the suture is substantially prevented and the anchor loop configuration of the distal end of the catheter is maintained. The anchor loop retains the desired positioning of the distal end of the catheter within the patient and minimizes inadvertent repositioning of the catheter during operation.

According to one embodiment of the present invention, the catheter hub includes a suture securement ridge. The suture securement ridge is adapted to secure the proximal portion of the suture extending from the catheter hub that may otherwise remain loose during the procedure. After the practitioner has rotated the rotatable lever handle to a secured position, the practitioner can then wind the proximal portion of the suture around the suture securement ridge. The practitioner then rotates the rotatable lever handle an additional amount in the secured position such that the rotatable lever handle contacts the suture securement ridge. This prevents unraveling of the proximal portion of the suture wrapped about the suture securement ridge.

Typically, once the drainage catheter is positioned at a desired location within the patient, the drainage catheter remains in the patient for a substantial period of time. According to one embodiment of the present invention, the rotatable lever handle and associated rotatable barrel can be depressed relative to the hub body to assume a locked configuration. The locked configuration prevents inadvertent rotational movement of the rotatable lever handle. As a result, inadvertent movement of the rotatable lever handle by movement of the patient, contact of the handle with clothing, the patient's bed, or other surface is prevented. The catheter hub can also include a release slot or release button that can be actuated by the practitioner by using a tool, such as a release tool, to release the locked configuration of the rotatable lever handle and allow for rotational movement of the rotatable lever handle. This allows the user to rotate the rotatable lever handle to the released position to manipulate the suture or withdraw the catheter.

The release tool can include a body that cooperatively engages with the hub and a release tab. The release tab can have a shape and size such that it can enter the release slot and unlock the rotatable handle lever. The release tool can also have a depression surface connected to the release tab such that when a practitioner presses on the depression surface, the release tab is pushed into the release slot to unlock the rotatable handle lever. In some configurations, the release tool can be secured to the hub, allowing the practitioner leverage to unlock the rotatable handle using only one hand. In other configurations, the release tool can include a hinge, allowing the tool to be positioned around the hub.

The release tool can also have a removal tool on an end of the release tool to aid the practitioner in removing a drainage tube from the catheter. The removal tool can have a portion that cooperates with a connector and a hub removal notch that cooperates with features on the connector to allow a practitioner additional leverage in loosening or tightening a drainage tube to the catheter. In some embodiments, the catheter and tool may come packaged together in a kit.

As will be appreciated by those skilled in the art, a variety of types and configurations of suture securement mechanisms can be utilized without departing from the scope and spirit of the present invention. For example, in one embodiment the rotatable lever handle is positioned to the side of the rotatable barrel rather than around the outer circumference of the catheter hub. In another embodiment, the distal end of the catheter forms other than a pigtail-type loop when in the anchor configuration. In another embodiment, the suture is utilized in connection with a release stylet such that the suture can be released by the rotatable lever handle or the stylet.

These and other aspects of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 8A is a cross-sectional side view of the catheter hub illustrating the manner in which the rotatable lever handle and the rotatable barrel allow movement of the suture when the rotatable lever handle is in a released position;

FIG. 8B is a cross-sectional side view of the catheter hub illustrating the manner in which the rotatable lever handle and the rotatable barrel secure the suture when the rotatable lever handle is in a secured position;

DETAILED DESCRIPTION OF EXEMPLARY EMBODIMENTS

The present invention relates to catheters. In particular, the present invention relates to a locking drainage catheter hub having a rotatable lever handle adapted to secure a suture thread. The secured suture thread maintains an anchor configuration of the distal end of the catheter. The anchor configuration secures the position of the catheter within the patient's body. The rotatable lever handle has a released position for allowing movement of the suture and a secured position for preventing movement of the suture. The rotatable lever may also be locked into the secured position by a locking mechanism. According to one embodiment of the present invention, the catheter hub includes a suture securement ridge adapted to secure the proximal portion of the suture that may otherwise remain loose during the procedure. According to one embodiment of the present invention, the rotatable lever handle and associated rotatable barrel can be locked by depressing the lever handle relative to hub body into a locked configuration to prevent inadvertent rotational movement of the rotatable lever handle and release of the suture. The catheter hub can also include a release slot or release button that can be actuated by the practitioner by hand, in the case of a button, or by using a tool, such as a release tool, to release the locked configuration of the rotatable lever handle and allow for rotational movement of the rotatable lever handle to release the suture. In some configurations, the catheter and a release tool can come packaged together in a kit.

Figure 1A:
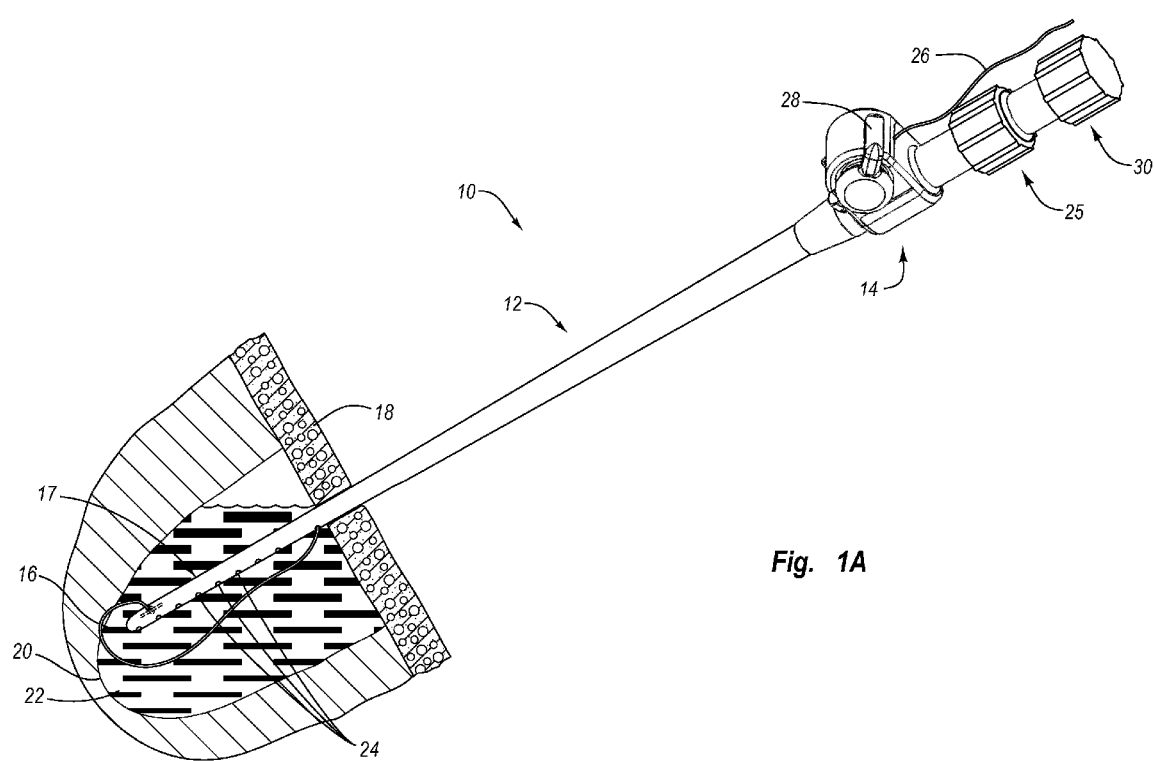
FIG. 1A is a perspective view of a drainage catheter illustrating a catheter hub having a rotatable lever handle in a released position and the catheter tip being introduced into a body cavity of a patient.
Figure 1B:
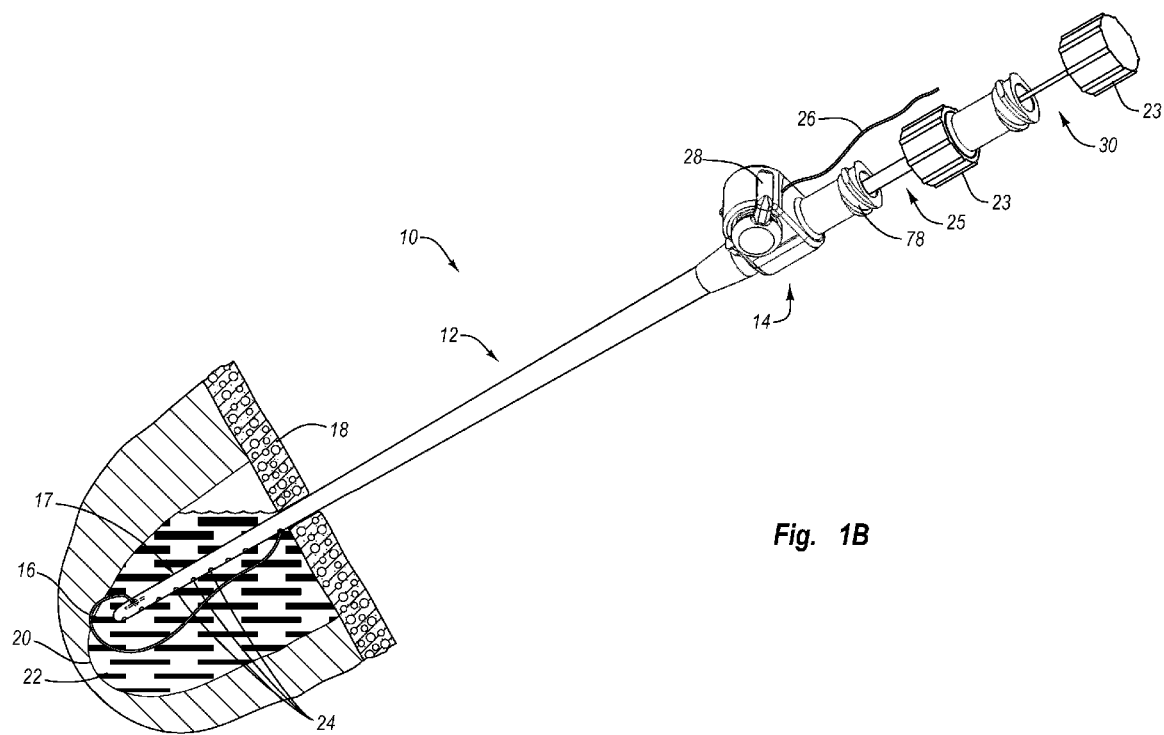
FIG. 1B is a perspective view of a drainage catheter illustrating a rigid member being removed from the catheter hub of FIG. 1A.

FIGS. 1A-1B are perspective views of drainage catheter 10 illustrating a catheter hub 14 having a rotatable lever handle 28 according to one embodiment of the present invention. Drainage catheter 10 is configured to be utilized for potentially prolonged periods to drain fluid from a patient. Catheter hub 14 and rotatable lever handle 28 provide a simple and effective mechanism to allow a user to selectively secure the anchor configuration of a distal end 17 of catheter tube 12 of drainage catheter 10. Rotatable lever handle 28 is adapted to secure a suture thread 26 to maintain the anchor configuration of a distal end of the catheter tube 12 so that the position of the catheter tube 12 is thereby secured within the patient's body. The rotatable lever handle 28 has a released position for allowing movement of the suture, and a secured position for preventing movement of the suture. Rotatable lever handle 28 is shown in the released position in FIG. 1A.

In the illustrated embodiment, catheter hub 14 is utilized in connection with catheter tube 12 of drainage catheter 10. Catheter tube 12 comprises an elongate tubular member having a drainage lumen for allowing the fluid to exit patient 18, entering catheter tube 12 through the distal end 17 of catheter tube 12. The configuration of catheter tube 12 allows fluids to be drained from a patient 18 to catheter hub 14. In the illustrated embodiment, distal end 17 is shown being introduced into a body cavity 20 of patient 18. During introduction, distal end 17 assumes a straightened configuration to facilitate the introduction of distal end 17 into a body cavity 20 of patient 18.

Distal end 17 is introduced into body cavity 20 at a position configured to optimize the drainage of the volume of fluid 22 from cavity 20. The distal end 17 can be introduced into the patient 18 through an existing lumen, or by insertion of a rigid member 25 into the lumen of the catheter tube 12 to allow correct positioning of the drainage catheter 10. In this example embodiment, the rigid member 25 can be attached to the drainage catheter 10 by engaging threaded connecting member 23 with threaded end 78. As illustrated in FIGS. 1A-1B, rigid member 25 is attached at one end to connecting member 23. As illustrated in FIGS. 1A-1B, rigid member 25 may include two members, one inside of the other, one having a blunt end (not shown) and having the approximate length of catheter tube 12 and contained entirely or substantially by catheter tube 12, and the other having a sharp end (not shown) that can extend beyond the tip 16 at the distal end 17 of the catheter tube 12 allowing the drainage catheter to be inserted directly into the patient 18. Alternatively, the rigid member 25 may be one member.

As illustrated in FIG. 1B, the rigid member 25 is removed from the catheter tube 12, clearing the lumen of catheter tube 12, after the distal end 17 of the catheter tube 12 is placed in the patient. A removal tool 86 (FIGS. 9A-12) may be used to loosen the rigid member 25 from threaded end 78. Embodiments of removal tools as part of a release tool are described in more detail below with respect to FIGS. 9A-11. In some embodiments, a kit for use by practitioners may include at least the drainage catheter 10, along with any combination of a blunt-ended rigid member 25, a sharp-ended rigid member 25, a release tool, and a removal tool (see FIGS. 9A-12).

A plurality of drainage bores 24 are positioned in the distal end 17 of catheter tube 12. The plurality of drainage bores permit the passage of fluids from cavity 20 to the lumen of catheter tube 12. The fluids can then flow along the length of catheter tube 12 and exit catheter hub 14. The fluids can then be passed to a biological disposal container or other disposal reservoir.

In the illustrated embodiment, suture 26 is utilized in connection with catheter tube 12 and catheter hub 14. Suture 26 is adapted to facilitate and maintain formation of an anchor loop configuration in distal end 17 of catheter tube 12. Suture 26 runs from catheter hub 14, along the length of catheter tube 12, exits catheter tube 12 at a suture exit bore 27, and is then secured to tip 16 of catheter tube 12. Catheter hub 14 enables securement or release of suture 26. Rotatable lever handle 28 is utilized to allow a user to either secure or release suture 26 during the procedure being performed. In FIGS. 1-1B, rotatable lever handle 28 is positioned in a released position. When rotatable lever handle 28 is in a released position, the practitioner can manipulate suture 26 so as to allow the straightening of distal end 17 of catheter tube 12 during introduction of distal end 17 into body cavity 20 of patient 18. When rotatable lever handle 28 is in a released position, the practitioner can also retract suture 26 to remove the slack in the portion of suture 26 adjacent distal end 17 of catheter tube 12.

As will be appreciated by those skilled in the art, a variety of types and configurations of drainage catheters can be utilized for draining bodily fluids from a patient without departing from the scope and spirit of the present invention. For example, in one embodiment, the fluids to be drained exit from a portion of the drainage catheter other than the catheter hub. In another embodiment, the drainage catheter 10 is adapted to be positioned adjacent an organ or in the vasculature of the patient. In another embodiment, the drainage catheter 10 is introduced utilizing a guidewire or rigid stylet.

Figure 2:
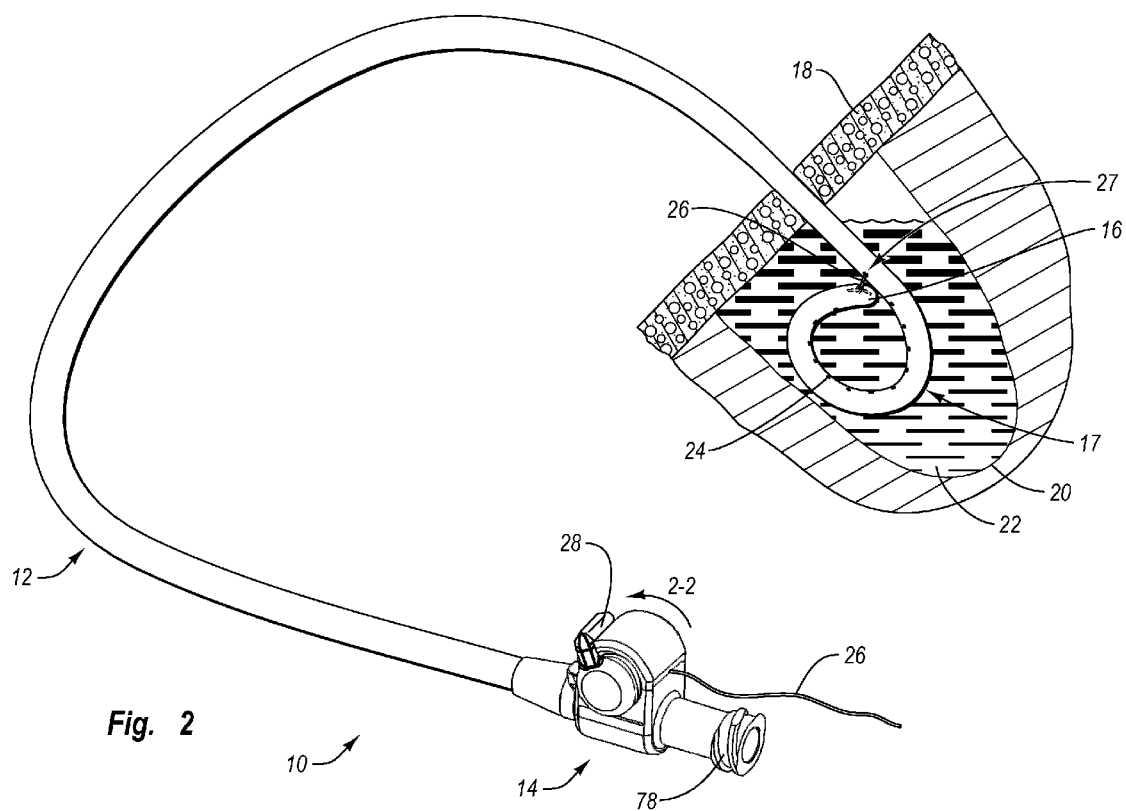
FIG. 2 is a perspective view of the drainage catheter of FIG. 1A illustrating the distal end of the catheter forming an anchor loop and the rotatable lever handle in a secured position.

FIG. 2 is a perspective view of drainage catheter 10 of FIG. 1A, illustrating distal end 17 of catheter tube 12 in an anchor loop configuration, and also illustrating rotatable lever handle 28 in a secured position. In the illustrated embodiment, distal end 17 of catheter tube 12 is positioned in a desired location within volume of fluid 22 in body cavity 20. When distal end 17 is positioned in a desired location within the volume of fluid 22, drainage of the volume of fluid 22 can be facilitated in an efficient and advantageous manner.

To maintain the desired positioning of distal end 17 within the body cavity 20 of patient 18, the practitioner grasps the free end of suture 26 extending from catheter hub 14. The user then pulls suture 26 in a rearward direction. Pulling suture 26 in a rearward direction draws tip 16 of catheter tube 12 to a suture exit bore 27. Suture exit bore 27 is a point on catheter tube 12 where suture 26 exits the side wall of catheter tube 12. Suture exit bore 27 is positioned proximally to catheter tip 16. As suture 26 draws tip 16 to suture exit bore 27, distal end 17 forms a pig-tail type anchor configuration. The anchor loop configuration in distal end 17 of catheter tube 12 maintains the position of distal end 17 in body cavity 20, even where the wall of body cavity is insufficiently rigid to secure traditional catheter securement devices.

Typically, once distal end 17 of catheter tube 12 is positioned in the anchor loop configuration, the drainage catheter 10 will remain positioned within the body of the patient for a considerable period of time to facilitate ongoing drainage of the volume of bodily fluid from the patient. Due to the considerable period of time drainage catheter 10 remains in operation, it is often desirable to maintain the anchor loop configuration of distal end 17 of catheter tube 12 for prolonged periods of time. To maintain the anchor loop configuration of distal end 17 of catheter tube 12, the user rotates rotatable lever handle 28 in the direction of directional arrows 2-2. Rotating rotatable lever handle 28 in the direction of directional arrows 2-2 moves rotatable lever handle 28 from the released position of rotatable lever handle 28 depicted in FIG. 1A to the secured position of rotatable lever handle 28 depicted in FIG. 2. When rotatable lever handle 28 is in the secured position, the components of catheter hub 14 secure suture 26, maintaining the tension on the portion of suture 26 positioned distally with respect to catheter hub 14. As a result, the user can release the portion of suture 26 extending from catheter hub 14, while maintaining the anchor loop configuration of distal end 17 of catheter tube 12.

In the illustrated embodiment, drainage bores 24 are positioned on the inside diameter of distal end 17 when distal end 17 is positioned in the anchor loop configuration. When drainage bores 24 are positioned on the inside diameter of distal end 17, contact by the walls of body cavity 20 on distal end 17 does not obstruct drainage of the volume of volume of fluid 22 from body cavity 20. This arrangement can be particularly helpful where the drainage of bodily fluid 22 causes collapse of the walls of body cavity 20 during operation of drainage catheter 10.

Figure 3:
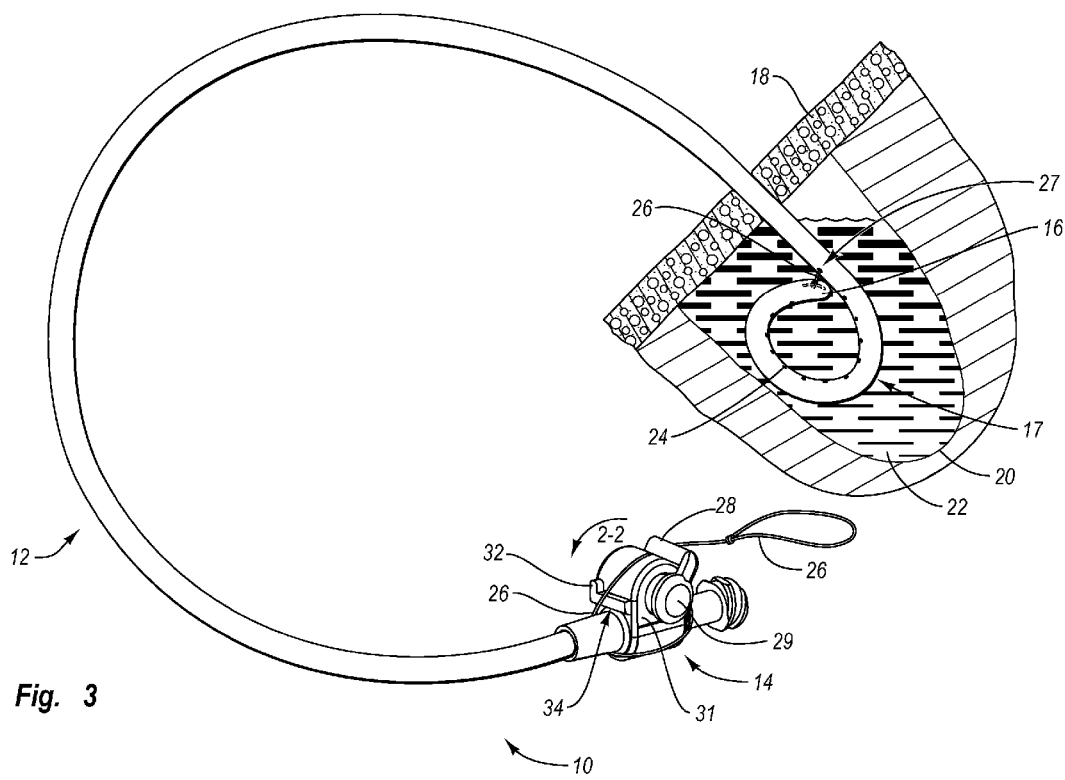
FIG. 3 is a perspective view of the drainage catheter of FIG. 1A illustrating a suture securement ridge of the catheter hub.

FIG. 3 is a perspective view of drainage catheter 10 illustrating the manner in which rotatable lever handle 28 can secure the portion of suture 26 extending proximally from catheter hub 14. In the illustrated embodiment, the orientation of the perspective view has been reversed to more clearly illustrate the components of catheter hub 14 that facilitate securing of the portion of suture 26 extending proximally from catheter hub 14. Once rotatable lever handle 28 has been rotated to the locked position the tension of suture 26 is secured. The practitioner can then release the portion of suture 26 extending proximally from catheter hub 14. However, in some circumstances, the length of the proximal portion of suture 26 can result in tangling of the proximal portion of suture 26 or other undesired interference with suture 26.

In the illustrated embodiment shown in FIG. 3, the proximal portion of suture 26 has been wrapped around a proximal end of catheter hub 14, and then extending under rotatable lever handle 28 and engaging with projection 32 and suture securement ridge 34. Projection 32 and suture securement ridge 34 are provided on the surface of catheter hub 14 adjacent the connection with catheter tube 12. Projection 32 and securement ridge 34 provide a simple and effective mechanism for securing the loose end of suture 26 when rotatable handle 28 is in a secured position. When the user is ready to remove or reposition anchor loop configuration of distal end 17 of catheter tube 12, the user simply unwraps the suture 26.

In the illustrated embodiment, a handle base 29 of rotatable handle 28 is shown. Handle base 29 provides a rotation axis about which the handle rotates. Additionally, the portion of handle 28 grasped by the practitioner is secured to the internal components of catheter hub 14 utilizing handle base 29. Handle base 29 has an amount of separation from a front surface of rotatable hub 14.

Figure 4:
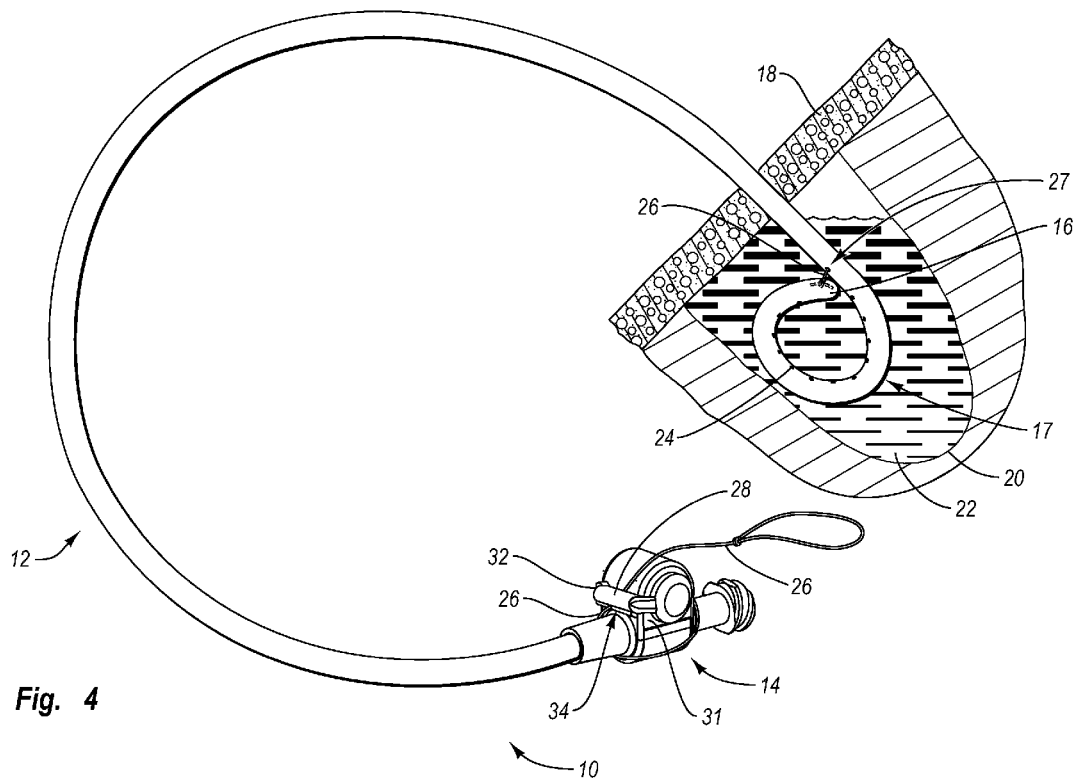
FIG. 4 is a perspective view of the drainage catheter of FIG. 1A illustrating the rotatable lever handle positioned adjacent the suture securement ridge to secure the proximal end of the suture.

FIG. 4 is a perspective view of drainage catheter 10 illustrating rotatable handle 28 in a locked configuration and positioned adjacent suture securement ridge 34. In the illustrated embodiment, when a user has wrapped the free proximal end of suture 26 about a proximal end of catheter hub 14, the user can utilize rotatable handle 28 to maintain the wrapped configuration of suture 26 by holding the loose end of suture 26 under rotatable handle 28 pressed against projection 32 and securement ridge 34. To utilize rotatable handle 28 to maintain the wrapped configuration of suture 26, the user rotates rotatable handle 28 in the direction of suture securement ridge 34. Rotatable handle 28 is configured to contact or be positioned in close proximity with one or both of projection 32 and suture securement ridge 34. In this position, rotatable handle 28 cooperates with securement ridge 34 to confine the wrapped portion of suture 26, preventing unraveling or slippage of suture 26. When rotatable handle 28 is rotated to the position depicted in FIG. 4, rotatable handle 28 is in the secured position.

In an alternative embodiment of the present invention, the user can wrap the suture 26 around another portion of drainage catheter 10, such as the hub 14, the catheter tube 12 or the catheter tube engagement member positioned between the catheter tube 12 and the body of the catheter hub 14. In this alternative embodiment, the tail of the suture can be threaded between the suture securement ridge and the rotatable handle such that the tail of the suture or other portions of the suture may be locked between the suture securement ridge and the rotatable handle when the rotatable handle is rotated to a locked position. In the embodiment, the rotatable handle is securely positioned adjacent the projection and in contact with the suture securement ridge and pushed into a locked configuration. To release the suture, the user moves the rotatable handle from a locked position, rotates the rotatable handle, and unwraps the suture from the catheter tube 12 or catheter tube engagement member.

In the illustrated embodiment, handle base 29 has been depressed such that it is flush with front surface 31 of catheter hub 14. When handle base 29 is depressed, rotatable handle 28 is locked in the secured position. When rotatable handle 28 is locked in the secured position, rotational forces exerted on rotatable handle 28 will not result in rotation of rotatable handle 28. This prevents inadvertent and undesired rotation of rotatable handle 28 when drainage catheter 10 is in operation. As a result, in the event that the rotatable handle 28 is inadvertently contacted by the patient's clothing, bed, chair or other surface the rotatable handle 28 will not be rotated to the released position. In a typical procedure, the practitioner depresses handle base 29 to a locked position when the anchor loop configuration of distal end 17 of catheter tube 12 is in a desired position, suture 26 has been wrapped about catheter hub 14, and rotatable lever handle 28 has been rotated to a position in which it covers the end portion of suture 26.

As will be appreciated by those skilled in the art, a variety of types and configurations of catheter hubs can be utilized without departing from the scope and spirit of the present invention. For example, in one embodiment only one of a suture securement ridge and a projection are provided with the catheter hub. In another embodiment, one or both the suture securement ridge and projection are provided on the side of catheter hub 14 opposite the catheter tube 12. In another embodiment, a locking member is provided to secure the suture relative to the securement ridge and the projection that is a separate and distinct component from the rotatable lever handle. In one embodiment, securement ridge and projection provide a groove, slot, taper, channel, or other relief surface to maintain the wrapped position of a free portion of suture. In another embodiment, a secondary mechanism independent of rotatable handle is utilized to lock the secured position of the rotatable handle.

Figure 5:
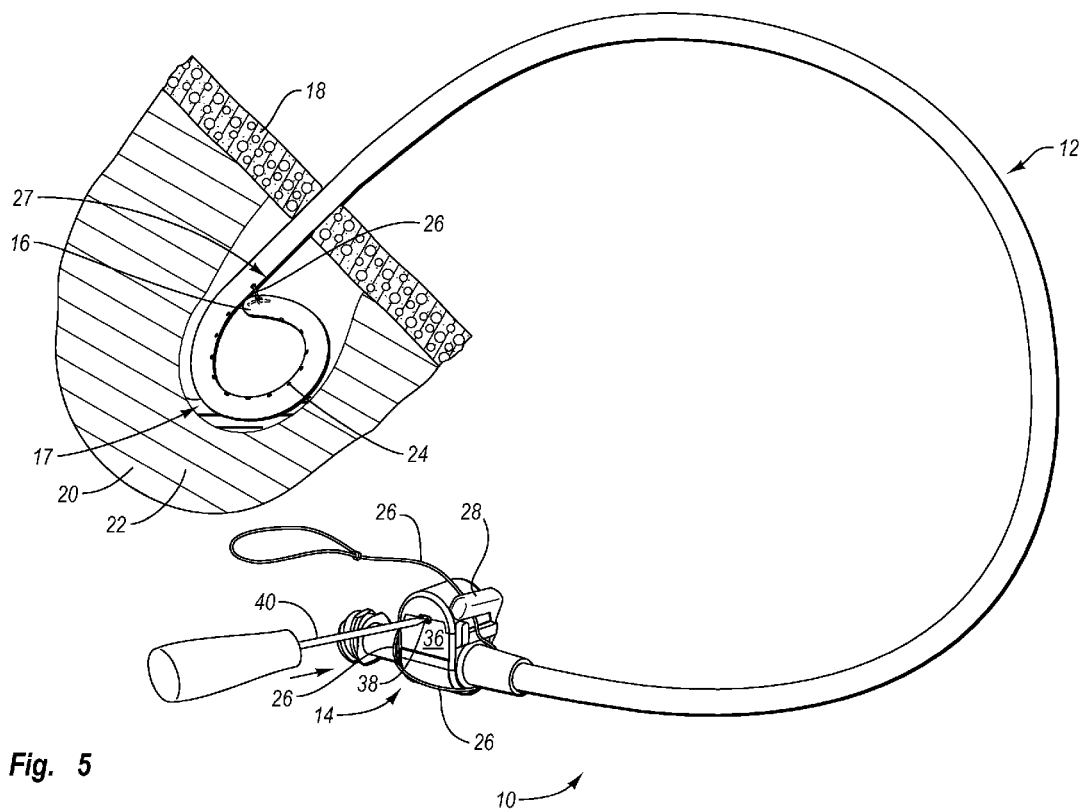
FIG. 5 is a perspective rear view of the drainage catheter of FIG. 1A illustrating a release slot allowing for moving the rotatable lever handle from a locked position to an unlocked position.

FIG. 5 is a rear-perspective view of catheter hub 14 illustrating a release slot 38 for unlocking the locked position of rotatable handle 28, thereby allowing rotation of rotatable lever handle 28. In the illustrated embodiment, the volume of fluid 22 in body cavity 20 has been substantially drained. Additionally, the size of body cavity 20 has greatly decreased due to the smaller amount of fluid exerting outward pressure on the walls of body cavity 20. As previously discussed, the anchor loop configuration of the distal end 17 of catheter tube 12 secures the position of distal end 17 in body cavity 20. Additionally, when rotatable handle 28 is in the secured position, the tension on suture 26 is maintained and the tip 16 of catheter tube 12 is secured adjacent suture exit bore 27. When tip 16 of catheter tube 12 is maintained adjacent suture exit bore 27, the anchor loop configuration of distal end 17 of catheter tube 12 is also maintained.

To release the anchor loop configuration of distal end 17 of catheter tube 12, the user must rotate rotatable handle 28 to a released position allowing movement of the length of suture 26. As discussed with reference to FIG. 4, when handle base 29 is depressed to a locked position, the user is prevented from rotating rotatable handle 28. A release slot 38 is provided on the rear surface 36 of catheter hub 14. The user can utilize release slot 38 to move handle base 29 laterally with respect to catheter hub 14 from the locked position to an unlocked position.

Release slot 38 allows a user to insert a pointed tool or other implement to move handle base 29 from a depressed locked position to a non-depressed unlocked position. In the illustrated embodiment, a practitioner is inserting the tip of a hemostat 40 into release slot 38. The tip of hemostat 40 or the tool or implement being utilized by the practitioner contacts a surface interior to release slot 38. The surface interior to release slot 38 conveys forces from the hemostat to handle base 29 to move handle base 29 from the locked position to the unlocked position. The user places a requisite amount of force on hemostat 40 to force handle base to the unlocked position. Once the requisite amount of force has been relayed from the surface interior to release slot 38, handle base 29 is moved to the non-depressed unlocked position and rotatable lever handle 28 can be rotated. The components of catheter hub 14 which operate in connection with handle base 29 and release slot 38 to provide locking and release of rotatable lever handle 28 will be discussed in greater detail with reference to FIGS. 6 and 7A. Other tools may be used to unlock the handle base 29 (See FIG. 3). Some examples of such tools are described in detail below with respect to FIGS. 9A-12.

As will be appreciated by those skilled in the art, a variety of locking and release mechanisms can be utilized to selectively secure the secured position of the rotatable lever handle. In one embodiment, a button is provided that can be pushed in a first direction to lock the secured position of the rotatable lever handle, and pushed in a second direction to allow rotational movement of the rotatable lever handle. In another embodiment, the user locks and unlocks the rotational position of the rotatable lever handle by exerting force directly on the rotatable lever handle. In one exemplary embodiment, the rotatable lever handle can be secured in more than one rotational position.

Figure 6:
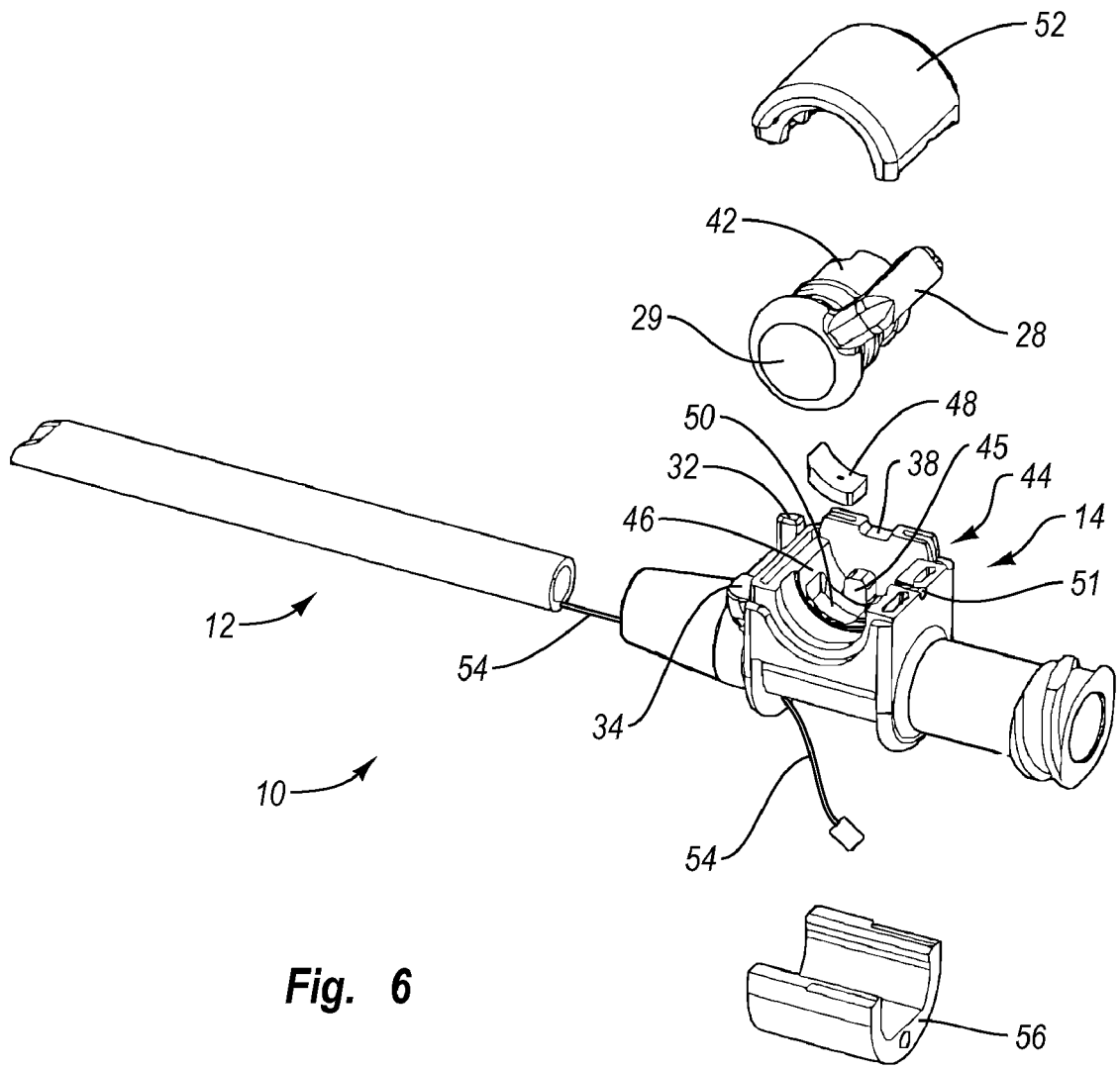
FIG. 6 is an exploded view of the catheter hub of FIG. 1A illustrating the components of the hub.

FIG. 6 is an exploded view of a catheter hub 14 illustrating the components of the catheter hub 14 including the rotatable barrel 42 utilized in connection with rotatable handle 28. In the illustrated embodiment, catheter hub 14 comprises a rotatable lever handle 28, a rotatable barrel 42, a hub body 44, a barrel seat 46, a suture seal 48, a suture seal seat 50, a suture channel 51, a housing 52, a stylet 54, and a stylet release member 56. Rotatable lever handle 28 is integrally coupled to rotatable barrel 42 utilizing handle base 29. Rotatable barrel 42 comprises a substantially cylindrically shaped member positioned perpendicularly to axis of catheter tube 12. Rotatable barrel 42 includes a cam surface (not shown) configured to selectively secure or release suture 26 (see FIG. 5) to secure the tension and/or positioning of suture 26. Rotatable barrel 42 and the cam surface will be discussed in greater detail with reference to FIG. 7A.

Hub body 44 comprises a securement mechanism for holding the internal components of catheter hub 14. Hub body 44 includes a body locking projection 45. Body locking projection 45 comprises a square or rectangular extension of the inner wall of hub body 44. Body locking projection 45 is sized to be positioned in a slot on the mating surface of rotatable barrel 42 when handle base 29 is depressed into a locked position. The mating interaction with body locking projection 45 and the slot in rotatable barrel 42 prevent rotational movement of rotatable barrel 42 and, thus, rotatable lever handle 28.

Release slot 38 is configured to cooperatively engage a projection of rotatable barrel 42 to prevent rotational movement of rotatable barrel 42. By utilizing release slot 38 and body locking projection 45 with the slot and projection of rotatable barrel 42 provides two points of securement for minimizing rotation of rotatable barrel 42. Release slot 38 allows a user to contact a rear surface or projection of rotatable barrel 42 to move handle base 29 to a non-depressed release position by using a tool or by a button that presses rotatable barrel 42 to an unlocked position. When the tool or implement is utilized by the user to contact the rear surface of rotatable barrel 42, rotatable barrel 42 is slid in the direction away from body locking projection 45. Some embodiments of tools that may be used to unlock the rotatable barrel 42 are described in more detail below in reference to FIGS. 9A-12. This slides the slot on the rear side of rotatable barrel 42 from cooperative engagement with body locking projection 45 allowing rotational movement of rotatable barrel 42. The rear relief surfaces of rotatable barrel 42 utilized in connection with release slot 38 and body locking projection 45 will be discussed in greater detail with reference to FIG. 7A.

Barrel seat 46 comprises a curved relief surface in hub body 44. Barrel seat 46 is sized to accommodate rotatable barrel 42 to allow for simple and advantageous rotation of rotatable barrel 42 relative to hub body 44. Barrel seat 46 and rotatable barrel 42 are configured to cooperatively engage suture 26 (not shown) to selectively secure suture 26 based on the rotational position of rotatable barrel 42. In one embodiment of the present invention, the barrel and barrel seat are comprised of smooth surface non-compressible materials such as acetyl, Delrin®, polycarbonate, or similar smooth surface materials. Suture seal 48 is configured to be positioned in suture seal seat 50 adjacent rotatable barrel 42.

Suture seal 48 provides a fluid tight seal with suture 26 to minimize the leakage of fluids from the main lumen of the catheter hub 14 as suture 26 passes from the main lumen of the catheter hub 14 to the suture seal seat 50. Suture channel 51 provides a passageway for suture 26 (not shown) from the interior of catheter hub 14 to the exterior of catheter hub 14.

A stylet 54 and stylet release member 56 are provided in connection with drainage catheter 10. Stylet 54 and stylet release member 56 are shown separated from one another for the sake of clarity. As will be appreciated by those skilled in the art, stylet 54 and stylet release member 56 are typically integrally coupled such that movement of stylet release member 56 results in movement of stylet 54. Stylet 54 runs from catheter hub 14 to distal end 17 of catheter tube 12. Stylet 54 provides a securement apparatus for suture 26. A variety of types and configurations of mechanisms can be utilized for providing a stylet and suture combination with a drainage catheter. In the illustrated embodiment, stylet 54 is positioned in a secondary lumen positioned in the sidewall of catheter tube 12. By utilizing a secondary lumen, materials that are drained through the primary lumen of catheter tube 12 do not interfere with proper operation of stylet 54. Stylet 54 and the secondary lumen run from catheter hub 14 to the tip 16 of the catheter tube 12. A small bore at the tip 16 of catheter tube 12 exposes stylet 54 and allows suture 26 to be wrapped around stylet 54.

When the practitioner is ready to remove drainage catheter 10 from the patient, the practitioner disengages stylet release member 56 from its coupling with catheter hub 14. As the user pulls stylet release member 56 in the rearward direction, stylet 54 begins to be withdrawn from the secondary lumen of catheter tube 12. Once stylet 54 is sufficiently withdrawn, stylet 54 is also withdrawn from the position in which it is engaged by suture 26. Since suture 26 is solely secured to the tip of catheter tube 12 utilizing stylet 54, removal of stylet 54 results in release of suture 26. When suture 26 is released, there is nothing to maintain the anchor configuration of distal end 17 of the catheter tube 12. As a result, as the user begins to withdraw distal end 17 of the catheter tube 12 from the patient 18, distal end 17 of the catheter tube 12 can straighten and easily exit the entry channel of catheter tube 12. Alternatively, the rigid member 25 may be extended into the catheter tube 12 to aid in straightening the catheter tube 12 for removal from the patient 18.

As will be appreciated by those skilled in the art, a variety of types and configurations of catheter hubs can be utilized without departing from the scope and spirit of the present invention. For example, in one embodiment the hub body includes two slots which cooperatively engage two projections of the rotatable barrel. In another embodiment, the rotatable barrel can be locked in a plurality of rotational positions. In another embodiment, the catheter hub does not include a stylet and stylet release member.

Figures 7A, 7B:
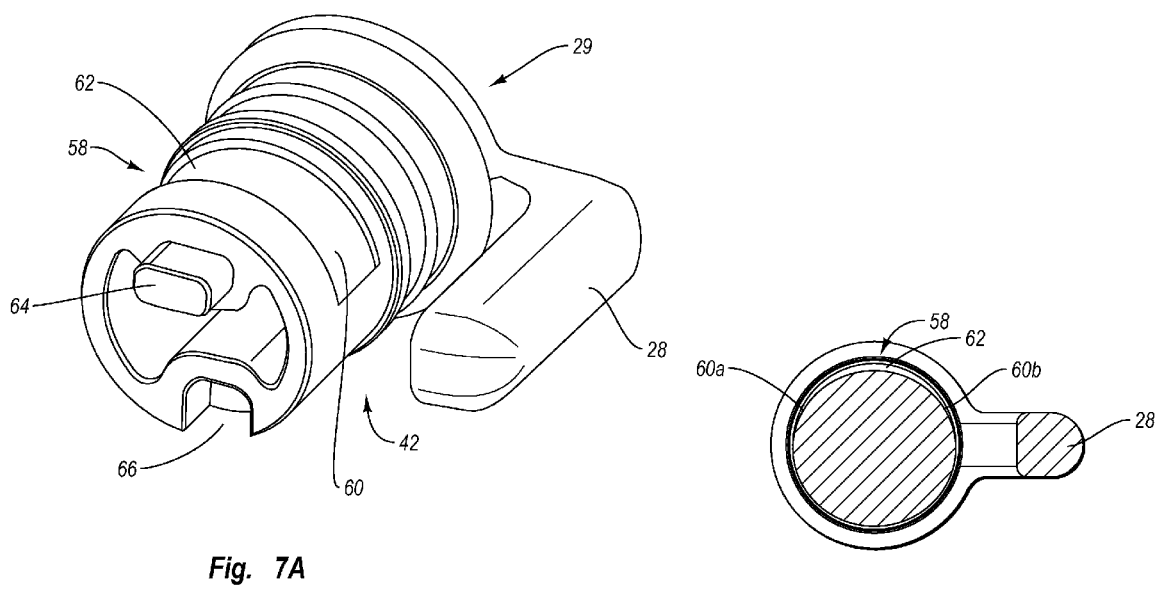
FIG. 7A is a close up perspective view illustrating a cam surface of the rotatable barrel utilized in connection with the rotatable lever handle.
FIG. 7B is a close-up end view of the rotatable barrel illustrating the relief of the cam surface relative to the outer circumference of the rotatable barrel.

FIG. 7A and FIG. 7B illustrate rotatable barrel 42 and rotatable lever handle 28 and a cam surface 58 associated therewith. Cam surface 58 is utilized with rotatable barrel 42 and rotatable lever handle 28 to release and secure suture 26 (not shown). In the illustrated embodiment, rotatable lever handle 28 is secured to rotatable barrel 42 utilizing handle base 29. Rotatable lever handle 28 can be grasped by a user and rotated to change the rotational position of rotatable barrel 42. Rotatable barrel 42 is one example of a cam means.

As will be appreciated by those skilled in the art, a variety of types and configurations of mechanisms for causing rotation of the rotatable barrel can be utilized without departing from the scope and spirit of the present invention. For example, in one embodiment a graspable projection that can be grasped by a user to rotate the rotatable barrel is provided on the face of handle base. In another embodiment, a tool is provided that cooperatively engages the rotatable barrel in a male/female relationship to allow a user to rotate the rotatable barrel.

Cam surface 58 includes a securement portion 60 and a release portion 62. Cam surface 58 extends inwardly from the outside diameter of the rotatable barrel 42 such that the release portion 62 of the cam surface 58 has a greater displacement from the inner contact surface of barrel seat 46 (see FIG. 6) than the securement portion 60. When the rotatable barrel 42 is rotated such that the suture is located between the release portion 62 and the barrel seat (not shown) the suture can be moved by the user. When the rotatable barrel 42 is rotated such that the suture is located between the securement portion 60 and the inner contact surface, the suture is cooperatively engaged between the barrel seat and securement portion 60 to prevent movement of the suture. In the embodiment illustrated in FIG. 7B securement portions 60*a* and 60*b* are positioned on both sides of release portion 62. Cam surface 58 is one example of a cam means.

In the illustrated embodiment, rotatable barrel 42 includes a barrel locking projection 64 and a barrel locking slot 66. Barrel locking projection 64 comprises an approximately rectangular shaped projection that extends from the rear surface of rotatable barrel 42. Barrel locking projection 64 is sized to be inserted into release slot 38 (see FIG. 6) of hub body 44 (see FIG. 6) when handle base 29 is depressed into a locking position. When handle base 29 is depressed into a locking position, barrel locking projection 64 slides into the release slot of the hub body effectively locking the rotational position of rotatable barrel 42. In the illustrated embodiment, locking projection 64 and release slot 38 (see FIG. 6) of hub body 44 (see FIG. 6) secure the rotational position of rotatable barrel 42 such that the suture is secured by securement portion 60 of cam surface 58. When a user desires to unlock the rotational position of rotatable barrel 42, the user inserts a tool or implement into release slot 38 (see FIGS. 6, 9A-12) and pushes locking projection 64 out of engagement with release slot 38. This allows the user to rotate rotatable barrel 42 utilizing rotatable lever handle 28.

Barrel locking slot 66 comprises an approximately square shaped slot which extends inward from the rear surface of rotatable barrel 42. Barrel locking slot 66 is sized to receive body locking projection 45 (see FIG. 6) of hub body 44 (see FIG. 6). When handle base 29 is depressed into a locking position, barrel locking slot 66 slides over the body locking projection of the hub body effectively locking the rotational position of the rotatable barrel 42. Barrel locking slot 66 and the body locking projection provide a secondary point of securement in addition to barrel locking projection 64 and the release slot to secure the rotational position of rotatable barrel 42. When the rotational position of rotatable barrel 42 is secured, the user is prevented from rotating rotatable lever handle 28. When a user pushes locking projection 64 out of engagement with release slot 38 utilizing a tool or other implement, the pushing force is relayed to the other components of rotatable barrel 42 sliding barrel locking slot 66 out of engagement with the body locking projection. The disengagement of barrel locking projection 64 and release slot 38 (see FIG. 6) combined with the disengagement of barrel locking slot 66 and body locking projection allow rotational movement of rotatable barrel 42. This allows the user to rotate rotatable lever handle 28 to the released position allowing movement of the suture and anchor configuration of the distal end 17 of the catheter tube 12.

As will appreciated by those skilled in the art, a variety of types and configurations of locking mechanisms can be utilized without departing from the scope and spirit of the present invention. For example, in one embodiment a spring loaded rotatable barrel that maintains a locked position configured to prevent rotation of the barrel is provided. The user depresses the rotatable barrel to disengage the locked position and rotate the barrel. When the user releases the rotatable barrel subsequent to rotation, the spring loaded configuration of the barrel again locks the barrel, securing the rotational position of the barrel. In another embodiment, a locking mechanism is provided having components that are separate from the rotatable barrel and the hub body. In another embodiment, the locking mechanism secures the rotational position of the rotatable barrel without depressing the handle base relative to the hub body. In another embodiment, the locking mechanism can secure a plurality of rotatable positions of the locking mechanism.

As will be appreciated by those skilled in the art, a variety of types and configurations of rotatable barrels and cam surfaces can be utilized without departing from the scope and spirit of the present invention. For example, in one embodiment, the entire circumference of the rotatable barrel comprises the cam surface and the cam surface is covered with alternating securement portions and release portions such that the rotatable barrel can be rotated continuously while providing alternating locking and releasing of the suture. In another embodiment, the suture is secured using a surface other than the cam surface. In yet another embodiment, a movable member other than the rotatable lever handle is provided to allow the user to selectively secure the suture.

FIGS. 8A and 8B are cross-sectional views of catheter hub 14 and catheter tube 12 depicting the manner in which rotatable barrel 42 secures suture 26. In the illustrated embodiments, catheter tube 12 is coupled to catheter hub 14 utilizing a catheter tube 12 at the distal end of catheter hub 14. The coupling of catheter hub 14 to catheter tube 12 positions a lumen of catheter tube 12 in fluid communication with a main lumen 68 of catheter hub 14. This allows bodily fluids to be drained from the patient, to the lumen of catheter tube 12, and then to main lumen 68 of catheter hub 14 before exiting drainage catheter 10.

Suture 26 is threaded along the length of the lumen of catheter tube 12 and into main lumen 68. As suture 26 passes through the lumen of catheter tube 12, suture 26 extends through main lumen 68. Suture 26 exits main lumen 68 through suture seal seat 50. From suture seal seat 50, suture 26 is threaded along the surface of barrel seat 46 before exiting through suture channel 51 (not shown).

FIG. 8A illustrates rotatable barrel 42 and rotatable lever handle 28 in a released portion. When rotatable barrel 42 is in the released position, release portion 62 of cam portion 58 is positioned adjacent the portion of suture 26 in contact with barrel seat 46. As previously discussed, cam surface 58 extends inwardly from the outside diameter of the rotatable barrel 42 such that the release portion 62 of the cam surface 58 has a greater displacement from the inner contact surface of barrel seat 46 than the securement portion 60. Due to the fact that rotatable barrel 42 is rotated such that suture 26 is located between the release portion 62 and the barrel seat 46, the suture 26 can be moved by the user.

FIG. 8B illustrates rotatable barrel 42 and rotatable lever handle 28 in a secured position. When the rotatable barrel 42 in the secured position the securement portion 60 of cam surface 58 is positioned adjacent the portion of suture 26 in contact with barrel seat 46. In this position, the suture is cooperatively engaged between barrel seat 46 and securement portion 60 effectively preventing movement of suture 26. The pathway of suture 26 provides both an effective conduit for suture 26 to the tip of catheter tube 12 while providing simple and effective manipulation of suture 26. Additionally, the juxtaposition of suture 26 and the components of catheter hub 14 allow a user to simply and efficiently secure the position of suture 26. By being able to secure and release the position of suture 26 the user can secure or release the anchor configuration of the distal end of the catheter tube 12 to position or remove the catheter tube 12 from the patient.

As will be appreciated by those skilled in the art, a variety of types and configurations of sutures can be utilized without departing from the scope and spirit of the present invention. For example, in one embodiment the stylet does not extend to the tip of the catheter tube. In this embodiment, the suture extends to the tip of the catheter tube, exits the catheter tube, and is threaded back to the position on the catheter tube where the stylet terminates to form the anchor configuration of the distal end of the catheter tube. In another embodiment, the suture is threaded from the tip of the catheter tube to the catheter hub in a side lumen positioned in the wall of the catheter tube. In another embodiment, the suture wraps around a majority of the circumference of the rotatable barrel before exiting the catheter hub. In another embodiment, the suture extends to the tip of the catheter tube, exits the catheter tube, and is threaded back to the position on the catheter tube where the second suture bore is located. The suture extends back through the main lumen to an anchor point in the catheter hub.

Figure 9A:
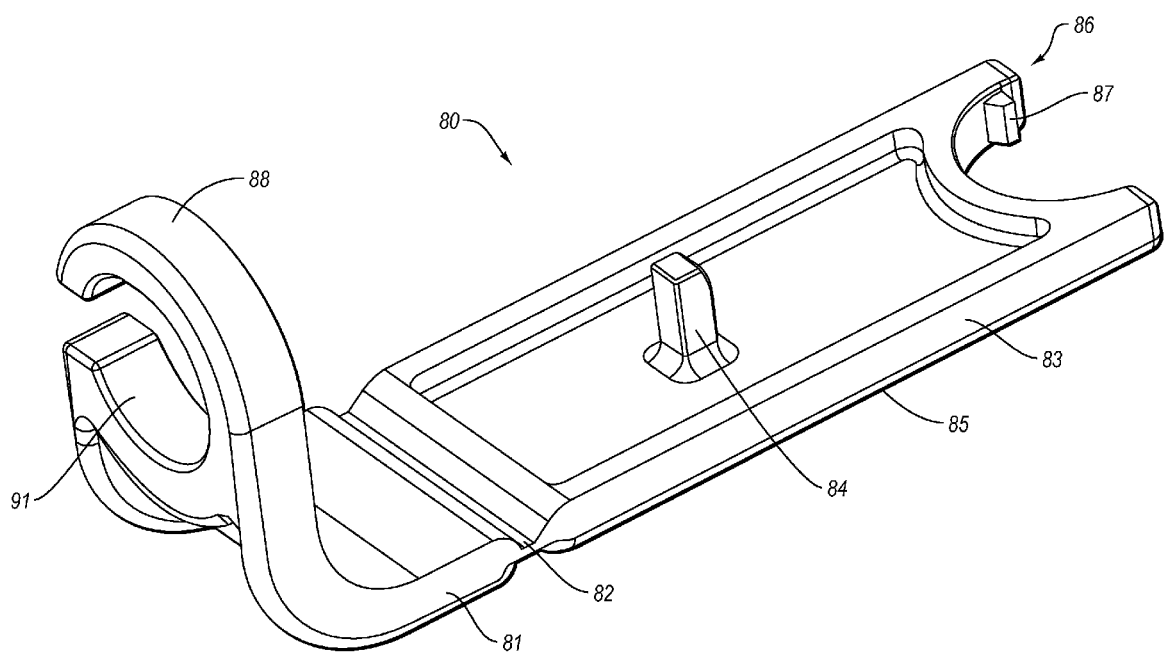
FIG. 9A is a perspective view of a tool for releasing the catheter hub when the catheter hub is in the locked position.
Figure 9B:
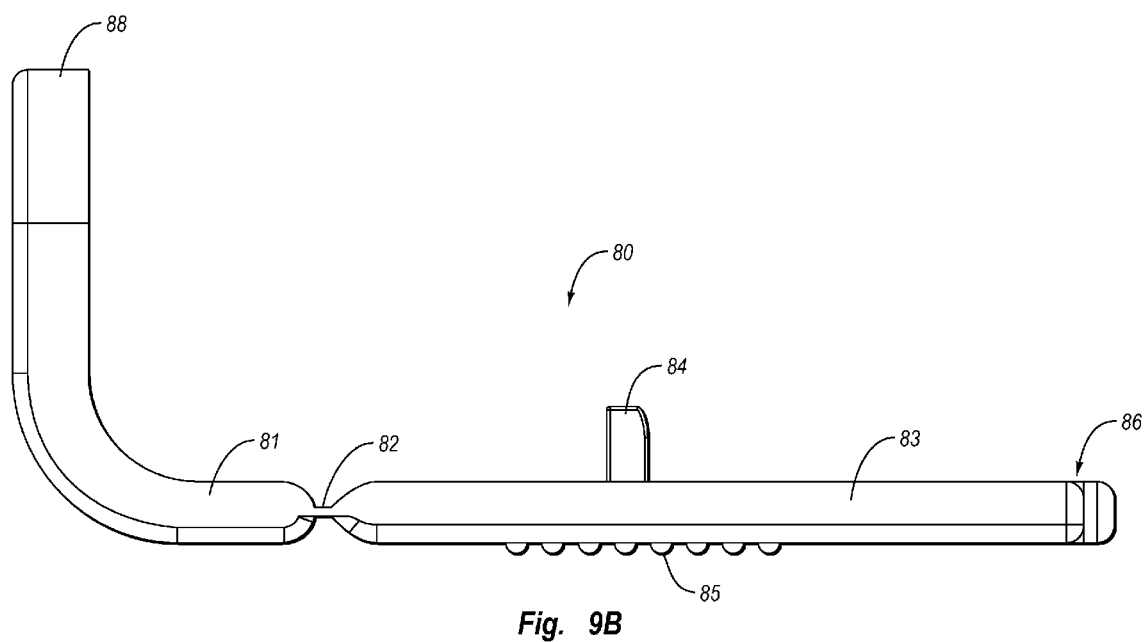
FIG. 9B is a side view of the tool illustrated in FIG. 9A.

FIGS. 9A and 9B illustrate one embodiment of a release tool 80 for unlocking rotatable lever handle 28. Additional embodiments of a release tool are illustrated in FIGS. 10A-12. Similar reference numerals have been used to refer to structures having similar functionality in the various embodiments. The release tools illustrated in FIGS. 9A-12 may be made from metal, plastic, or any other suitable material.

To unlock rotatable lever handle 28, a practitioner positions release tab 84 into release slot 38 and positions end 88 near rotatable lever handle 28 such that cutout 91 substantially encircles handle base 29. The release tool 80 bends elastically at hinge 82, allowing the release tool 80 to conform to the catheter hub 14. When the release tool 80 is positioned, the practitioner can press depression surface 85 on body member 83, which then presses release tab 84 into slot 38, unlocking rotatable lever handle 28. The release tool 80 can then be removed from the catheter hub 14, allowing the practitioner to move rotatable lever handle 28 to the released position to adjust the suture 26, or remove drainage catheter 10 as discussed previously.

The body member 83 of the release tool 80 can also include a removal tool 86. The removal tool 86 can be used by the practitioner to remove stylet release member 56 (as shown in FIG. 6) from catheter hub 14, allowing release of the suture as described above. To remove stylet release member 56, removal tool 86 is held by a practitioner such that removal notch 87 engages in the joint between the stylet release member 56 and catheter hub 14, causing stylet release member 56 to become separated from catheter hub 14.

Removal tool 86 may also be used to loosen a drainage tube (not shown) or rigid member 25 from the threaded end 78 of drainage catheter 10. The removal tool 86 can be cooperatively engaged with a connector for connecting a drainage tube to the drainage catheter 10. Connectors, such as connector 23 of rigid member 25, include exterior ridges to facilitate tightening or removal from threaded end 78. Removal notch 87 may be engaged with the exterior ridges of a connector attached to threaded end 78 to give added leverage in removing the connector.

Figure 10A:
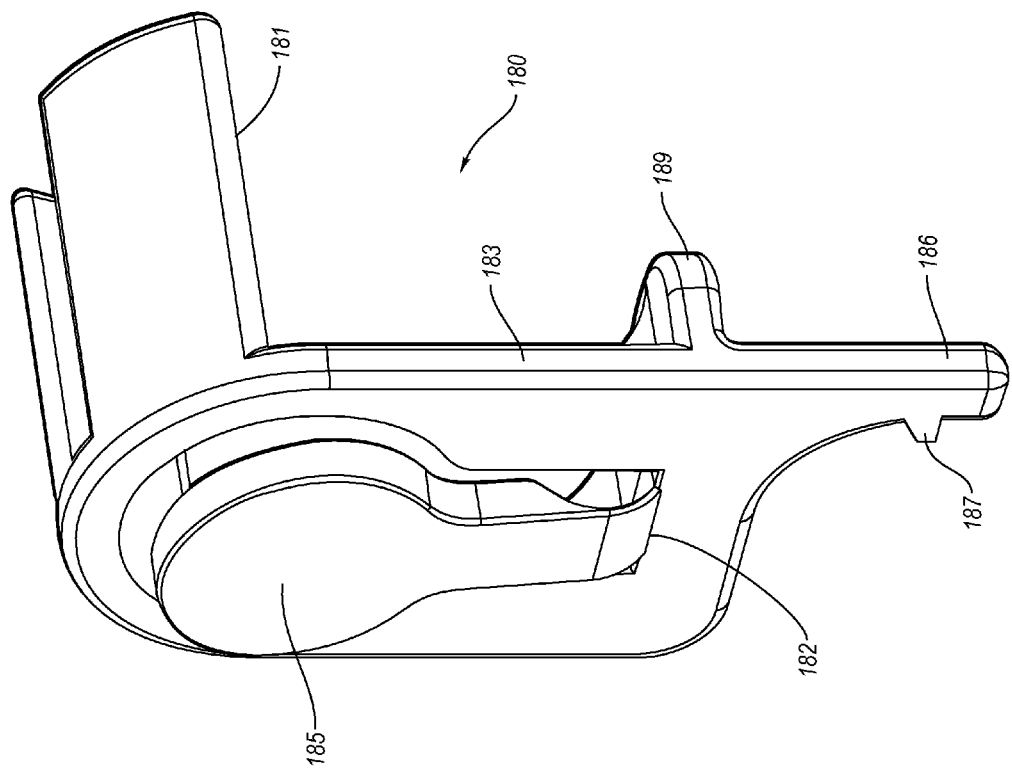
FIG. 10A is a perspective view of a tool for releasing the catheter hub when the catheter hub is in the locked position.
Figure 10B:
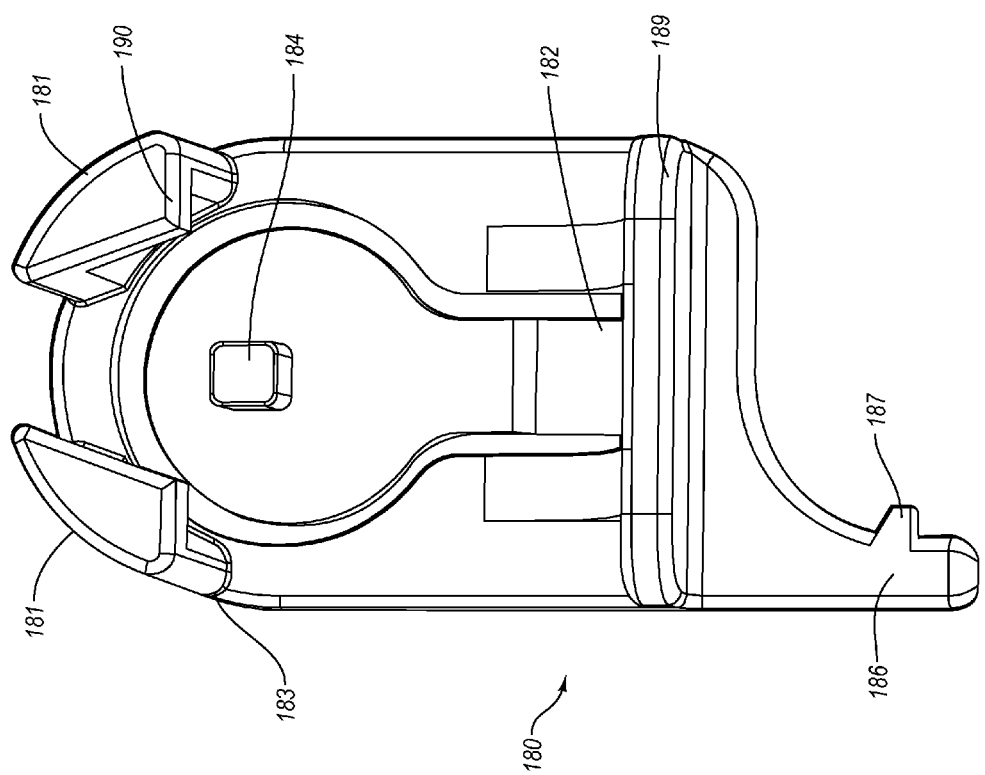
FIG. 10B is a rear perspective view of the tool illustrated in FIG. 10A.

FIGS. 10A-10B illustrate another embodiment of a release tool 180 for unlocking the rotatable lever handle 28. In this embodiment, depression surface 185 is attached to body member 183 with hinge 182. Release tab 184 is located opposite to depression surface 185, such that when depression surface 185 is pressed by a practitioner, the release tab 184 moves with respect to body member 183 by hinge 182. An engagement ridge 189, engagement arms 181, and engagement tabs 190 cooperate to conform to the catheter hub 14, such that the release tab 184 is positioned into release slot 38. Engagement tabs 190 hold the body member 183 securely against the catheter hub 14. When placing release tool 180 over the catheter hub 14, the engagement arms 181 flex to allow engagement tabs 190 to slide over and securely attach to the catheter hub 14. When the release tool 180 is positioned, the practitioner can press depression surface 185 with respect to the body member 183 and the catheter hub 14, which then presses release tab 184 into slot 38 unlocking rotatable lever handle 28. The release tool 180 can then be removed from the catheter hub 14, allowing the practitioner to move the rotatable lever handle 28 to the released position to adjust the suture 26, or remove drainage catheter 10 as discussed previously.

Similar to release tool 80, the body member 183 of the release tool 180 can also include a removal tool 186. The removal tool 186 includes removal notch 187, and can be used in the same manner as described above with respect to removal tool 86.

Figure 11:
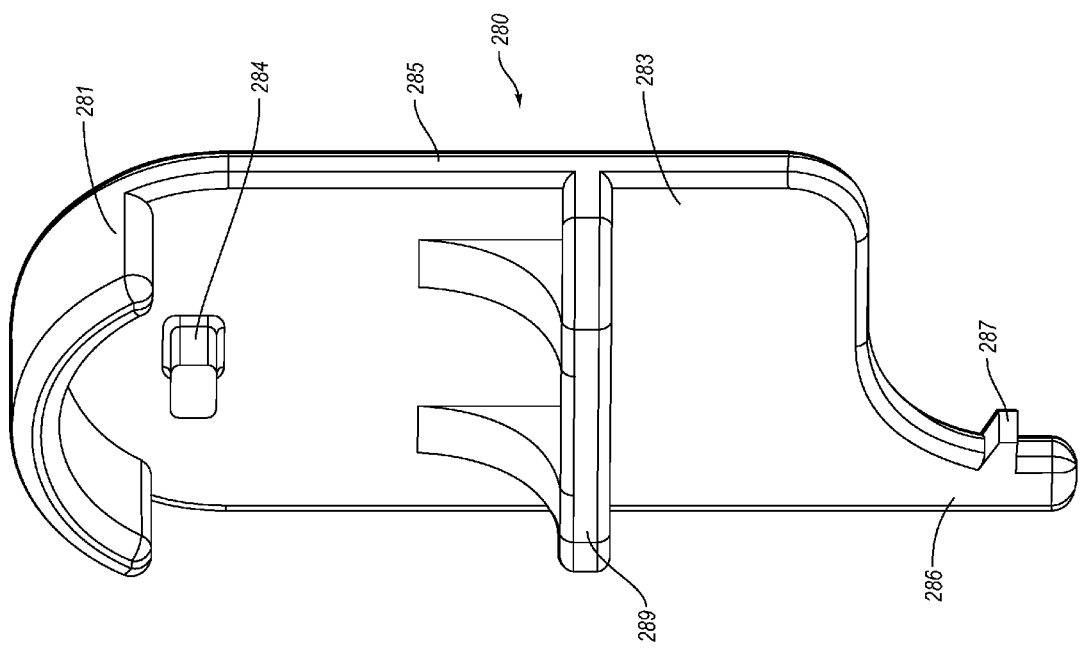
FIG. 11 is a perspective view of a tool for releasing the catheter hub when the catheter hub is in the locked position.

FIG. 11 illustrates another embodiment of a release tool 280 for unlocking the rotatable lever handle 28. This embodiment is substantially similar to release tool 180 of FIGS. 10A-B. One difference, however, is that release tool 280 does not have engagement tabs on engagement arm 281, and does not have a hinge. A practitioner positions the release tool 280 proximate to catheter hub 14, such that the release tab 284 engages in release slot 38. The practitioner then presses on depression surface 285, holding a portion of catheter hub 14, to allow rotatable lever handle to unlock.

Similar to release tools 80 and 180, the body member 283 of the release tool 280 can also include a removal tool 286. The removal tool 286 includes removal notch 287, and can be used in the same manner as described above with respect to removal tools 86 and 186.

Figure 12:
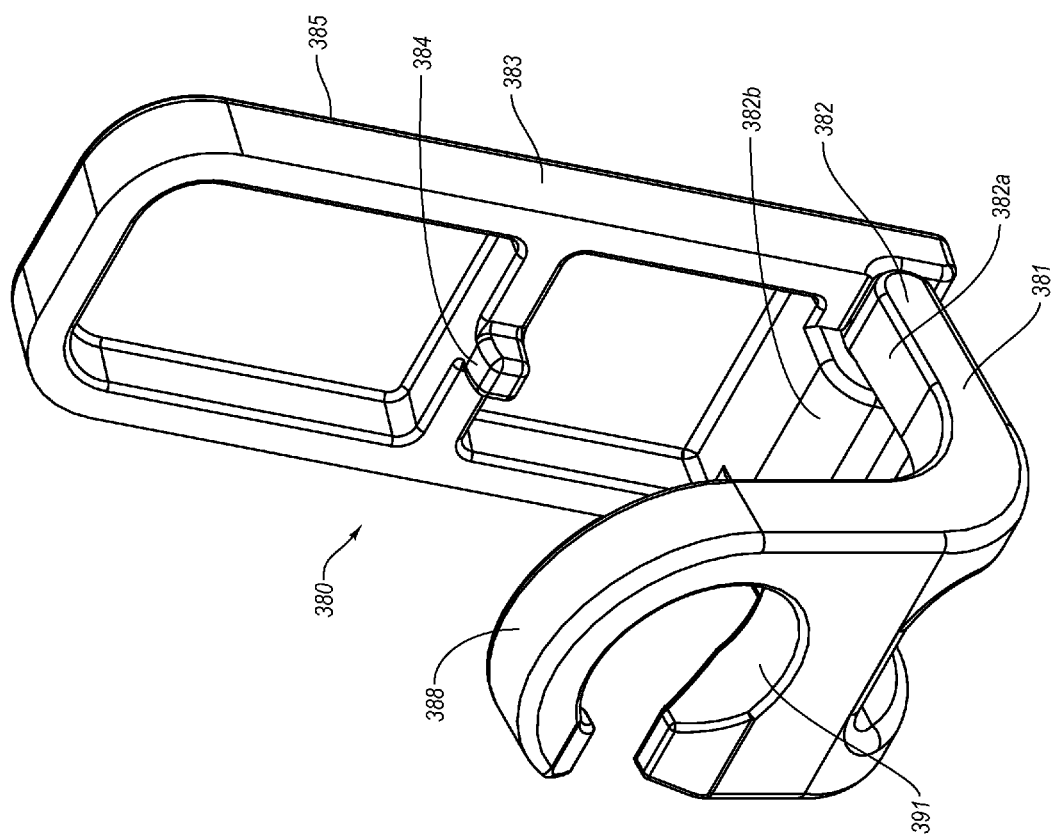
FIG. 12 is a perspective view of a tool for releasing the catheter hub when the catheter hub is in the locked position.

FIG. 12 illustrates another embodiment of a release tool 380 for unlocking rotatable lever handle 28. To unlock rotatable lever handle 28, a practitioner positions release tab 384 into release slot 38 and positions end 388 near rotatable lever handle 28 such that cutout 391 substantially encircles handle base 29. The release tool 380 bends at hinge 382, allowing the release tool 380 to conform to the catheter hub 14. More particularly, hinge 382 allows release tab 384 to be positioned as necessary to unlock rotatable lever handle 28. Hinge 382 is a pin-type hinge with hinge members 382a and 382b. Hinge members 382a are located on engagement arms 381, and hinge member 382b is located on body member 383. When the release tool 380 is positioned, the practitioner can press depression surface 385 on body member 83, which then presses release tab 384 into slot 38 unlocking rotatable lever handle 28. The release tool 380 can then be removed from the catheter hub 14, allowing the practitioner to move rotatable lever handle 28 to the released position to adjust the suture 26, or remove drainage catheter 10 as discussed previously.

As will be appreciated by those skilled in the art, a variety of types and configurations of release tools can be utilized without departing from the scope and spirit of the present invention. For example, in one embodiment the release tool does not include a removal tool. In this embodiment, a removal tool may be a separate tool.

In some embodiments, the locking hub may lock using a variety of means. For example, the hub may simultaneously hold the suture from moving and lock with a single action, which may then be unlocked using the release tool. Single actions to lock the hub may include a button, a sliding lock that responds to a particular motion of the suture, a rotating handle that automatically locks upon reaching a secured position, or other single-action locking mechanisms.

In some embodiments, a release tool and/or a removal tool may be connected to a portion of the drainage catheter to make the release tool and/or removal tool more accessible to a practitioner, and to reduce the risk of loss. For example, a release tool with an integrated removal tool may be connected to a small eyelet on a portion of the catheter with a small lanyard. Alternatively, the release tool may include a securing implement such as a hook and loop type fastener, or an adhesive patch to secure the release tool a portion of the catheter, or to a surface or other suitable item near the drainage catheter such as a table, bed, or tubing.

In other embodiments, a kit according to the present invention may also include additional tubing, sterile gloves, sterilization pads, additional members configured to be inserted into the drainage catheter such as diagnostic testing implements or devices, structural support elements, or other devices and implements used in conjunction with drainage catheters.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter kit, comprising:
   a drainage catheter including;
      a tube;
      a hub body attached to the tube;
      a seat having a substantially circular inner contact surface adapted to be in contact with a length of the suture; and
         a rotatable barrel adapted to be positioned in the seat such that the rotatable barrel is positioned perpendicular to the axis of the catheter tube, the rotatable barrel having a substantially circular contact surface, the outside diameter configured to remain in contact with the inner contact surface of the seat during rotation of the rotatable barrel wherein the rotatable barrel includes a cam connected to the hub body and being rotatable between a first position and a second position, wherein the cam is configured to secure a suture when in the first rotational position, and allow movement of the suture along the tube when in the second position wherein the length of suture is cooperatively engaged between the rotatable barrel and the inner contact surface of the seat at least when the cam is in the first position;
      a handle connected to the cam, wherein the rotatable lever handle is configured to move the cam between the first position and the second position; and a locking mechanism associated with the rotatable barrel, wherein the locking mechanism is configured to secure the rotational orientation of the rotatable barrel when the locking mechanism is in a locked position; and a release tool configured to unlock the locking mechanism, wherein the tool includes: at least one engagement portion configured to facilitate positioning of the release tool with respect to the hub body, and a release portion configured to operate the locking mechanism.

2. The catheter kit of claim 1, wherein the locking mechanism is integrally formed on at least one of the cam and the hub body.

3. The catheter kit of claim 2, wherein the locking mechanism secures the handle in the first position.

4. The catheter kit of claim 1, wherein the locking mechanism includes a release slot formed in the hub body, the release slot being configured to allow a user to disengage the locking mechanism.

5. The catheter kit of claim 4, wherein the release portion is a release tab configured to be inserted within the release slot.

6. The catheter kit of claim 1, wherein the release portion is configured to engage the handle to move the handle in a reverse lateral direction relative to the hub body to unlock the locking mechanism.

7. The catheter kit of claim 1, further comprising a device configured to be releasably engaged with the drainage catheter tube.

8. The catheter kit of claim 7, further comprising a removal tool configured to engage and separate a portion of the drainage catheter.

9. The catheter kit of claim 8, wherein the removal tool comprises a portion of the release tool.

10. The catheter kit of claim 1, wherein the release tool includes a hinge connecting the first engagement portion and the second engagement portion.

11. A catheter kit, comprising:
a drainage catheter, the drainage catheter including:
a tube;
a locking catheter hub comprising:
a hub body attached to the tube;
a seat having a substantially circular inner contact surface adapted to be in contact with a length of the suture; and
a rotatable barrel adapted to be positioned in the seat such that the rotatable barrel is positioned perpendicular to the axis of the catheter tube, the rotatable barrel adapted to be in contact with the length of the suture, the rotatable barrel having a substantially circular outside diameter, the outside diameter forming a substantially circular contact surface, the outside diameter configured to remain in contact with the seat wherein the contact between the substantially circular inner contact surface of the seat and the substantially circular outside diameter of the rotatable barrel provides a sliding surface to allow rotation of the rotatable barrel relative to the other components of the drainage catheter hub such that the suture is secured when the rotatable barrel is in a first position and the suture is allowed to move when the rotatable barrel is in a second position;
a locking mechanism associated with the rotatable barrel and being adapted to secure the rotational position of the rotatable barrel when the locking mechanism is in a locked position; and a release tool configured to unlock the locking hub, the release tool including:
a first engagement portion configured to interface with the locking catheter hub to facilitate positioning of the release tool with respect to the locking catheter hub; and
a second engagement portion configured to engage a portion of the locking catheter hub to unlock the locking hub to release to the locking mechanism and allow rotation of the rotatable barrel.

12. The catheter kit of claim 11, wherein the release tool includes a first body portion, a second body portion, and a hinge rotatably coupling the first body portion to the second body portion.

13. The catheter kit of claim 12, wherein the second engagement portion is a tab extending from the first body portion.

14. The catheter kit of claim 12, wherein the first engagement portion is located on the second body portion, wherein the first engagement portion is configured to engage a handle associated with the rotatable barrel.

15. The catheter kit of claim 11, further comprising a secondary device configured to be connected to the tube of the catheter, and
wherein the release tool further includes a projection configured to assist in separation of at least a portion of the secondary device from the tube of the catheter.

16. A drainage catheter comprising:
a tube;
a hub body attached to the tube;
a seat having a substantially circular inner contact surface adapted to be in contact with a length of the suture; and
a rotatable barrel adapted to be positioned in the seat such that the rotatable barrel is positioned perpendicular to the axis of the catheter tube, the rotatable barrel adapted to be in contact with the length of the suture, the rotatable barrel comprising;
a substantially circular outside diameter, the outside diameter forming a substantially circular contact surface, the outside diameter configured to remain in contact with substantially the entire inner contact surface of the seat wherein the contact between the substantially circular inner contact surface of the seat and the substantially circular outside diameter of the rotatable barrel provides a sliding surface to allow rotation of the rotatable barrel relative to the other components of the drainage catheter hub; and
a cam, the cam having an engagement portion configured to cooperatively secure the suture between the rotatable barrel and the inner contact surface of the seat; and a release portion configured to allow movement of the suture between the rotatable barrel and the inner contact surface of the seat; and
a rotatable lever handle connected to the rotatable barrel, wherein the actuation of the rotatable lever handle moves the rotatable barrel between a first position in which the suture is positioned between the release portion and the inner contact surface and second position in which the suture is positioned between the engagement portion and the inner contact surface of the seat.

* * * * *